United States Patent
Reiter et al.

(10) Patent No.: US 10,279,158 B2
(45) Date of Patent: *May 7, 2019

(54) DISPOSABLE CONNECTOR FOR HEMOFILTRATION

(71) Applicant: Fresenius Medical Care Deutschland GmbH, Bad Homburg (DE)

(72) Inventors: Reinhold Reiter, Crema (IT); Massimo Fini, Mirandola (IT); Andrea Vaiano, Merate (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 391 days.

This patent is subject to a terminal disclaimer.

(21) Appl. No.: 15/084,520

(22) Filed: Mar. 30, 2016

(65) Prior Publication Data

US 2016/0271383 A1 Sep. 22, 2016

Related U.S. Application Data

(63) Continuation of application No. 13/808,683, filed as application No. PCT/EP2011/060314 on Jun. 21, 2011, now Pat. No. 9,352,139.

(30) Foreign Application Priority Data

Jul. 6, 2010 (EP) .................................... 10168559

(51) Int. Cl.
| | | |
|---|---|---|
| A61M 39/10 | (2006.01) | |
| A61M 39/06 | (2006.01) | |
| F16L 55/00 | (2006.01) | |
| A61M 1/36 | (2006.01) | |

(52) U.S. Cl.
CPC ............ *A61M 39/10* (2013.01); *A61M 1/367* (2013.01); *A61M 39/06* (2013.01); *F16L 55/00* (2013.01); *A61M 2039/1027* (2013.01); *A61M 2039/1077* (2013.01); *Y10T 137/9029* (2015.04)

(58) Field of Classification Search
CPC .......... A61M 1/367; A61M 2039/1027; A61M 2039/1077; A61M 39/06; A61M 39/10; F16L 55/00; Y10T 137/9029
See application file for complete search history.

(56) References Cited

U.S. PATENT DOCUMENTS

| | | | |
|---|---|---|---|
| 4,781,702 | A | 11/1988 | Herrli |
| 5,501,426 | A | 3/1996 | Arkinson et al. |
| 2003/0158539 | A1 | 8/2003 | Bouphavichith et al. |
| 2008/0093571 | A1 | 4/2008 | Desecki |
| 2008/0303267 | A1 | 12/2008 | Schnell et al. |

(Continued)

FOREIGN PATENT DOCUMENTS

| | | |
|---|---|---|
| CA | 1191413 | 8/1985 |
| EP | 1181946 | 2/2002 |
| EP | 2059279 | 5/2009 |

(Continued)

*Primary Examiner* — John Kim
(74) *Attorney, Agent, or Firm* — Jacobson Holman, PLLC.

(57) ABSTRACT

A disposable connector suitable for engagement on a substitution port of a hemofiltration machine includes a main body defining a duct, and a pliable element that engages an end of the main body. The pliable element includes a membrane occluding the duct and performing a valve function, and a seal portion radially expanding outward of the duct.

21 Claims, 8 Drawing Sheets

(56) References Cited

U.S. PATENT DOCUMENTS

2010/0087772 A1    4/2010   Gronau et al.

FOREIGN PATENT DOCUMENTS

| JP | 59155255 | 9/1984 |
|---|---|---|
| JP | 631894 | 1/1988 |
| JP | 2009006051 | 1/2009 |
| WO | WO 2008/150781 | 12/2008 |

PRIOR ART

DISPOSABLE CONNECTOR FOR HEMOFILTRATION

CROSS-REFERENCE TO RELATED APPLICATIONS

This application is a continuation of U.S. application Ser. No. 13/808,683, filed Jan. 7, 2013, now allowed, the disclosure of which is incorporated by reference as is fully set forth herein. The aforementioned U.S. application Ser. No. 12/734,977 is a nationalization of PCT/EP2011/060314 filed Jun. 21, 2011.

BACKGROUND OF THE INVENTION

1. Field of Invention

The invention concerns a disposable connector intended to be used for medical purposes; in particular a connector intended to be used during hemofiltration and/or hemodiafiltration treatments.

2. Description of the Prior Art

Hemodialysis treatments require an extracorporeal blood circulation. The blood circuit comprises an out-tube intended to supply blood from the patient to the hemodialysis machine, where blood is passed through a filter in order to remove waste products. The blood circuit further comprises an in-tube intended to supply filtered blood from the hemodialysis machine back to the patient.

Most of the recent hemodialysis machines are designed to perform also the so called hemofiltration and/or hemodiafiltration treatments. Hemofiltration treatment implies the removal of some waste water from the blood and, accordingly, it needs also to compensate the removal by means of the addition of saline solution, i.e. the so called substitution liquid. Where such treatment is combined with a traditional hemodialysis, the so called hemodiafiltration treatment is obtained. In the following, for sake of simplicity, with the term "hemofiltration" reference will be made both to the actual hemofiltration and to the hemodiafiltration treatments.

Figure 1:
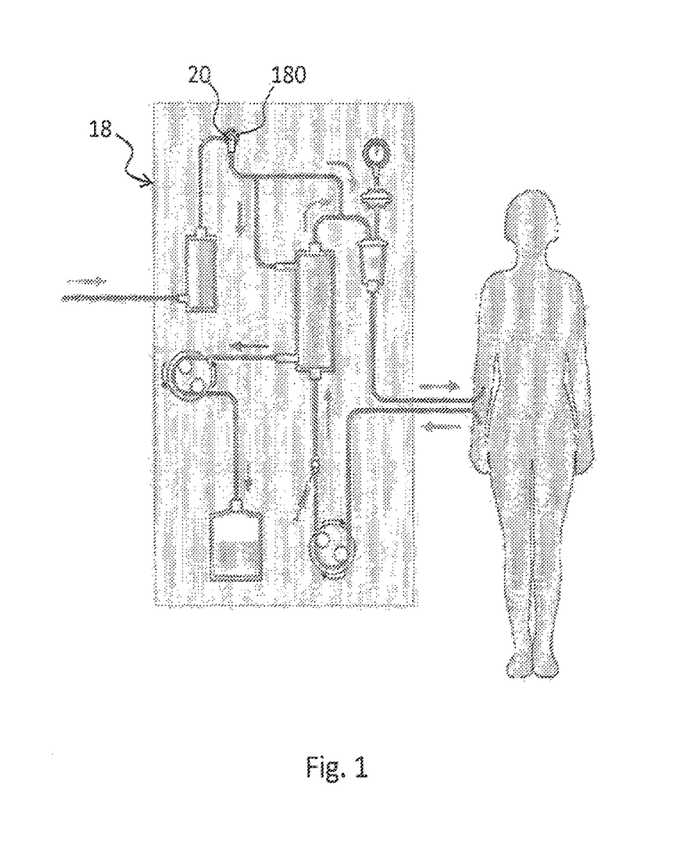
FIG. 1 schematically represents a hemofiltration machine and the related extracorporeal circuit used in a hemofiltration treatment of a patient's blood.

Such recent hemodialysis machines further need a substitution line intended to supply the substitution liquid in the blood flow directed to the patient. According to some machines, for example the one disclosed in EP 2 059 279, the substitution line is obtained from the water system (see FIG. 1). In particular, water coming from the water system is subjected to an ultrafiltration treatment by the machine itself, then in the ultrafiltered water salts are dissolved which are needed for making it a physiological solution usable as a substitution liquid. Thus the machine comprises a port (shown in detail in FIGS. 2 and 3) intended to supply the substitution liquid.

Figure 4:
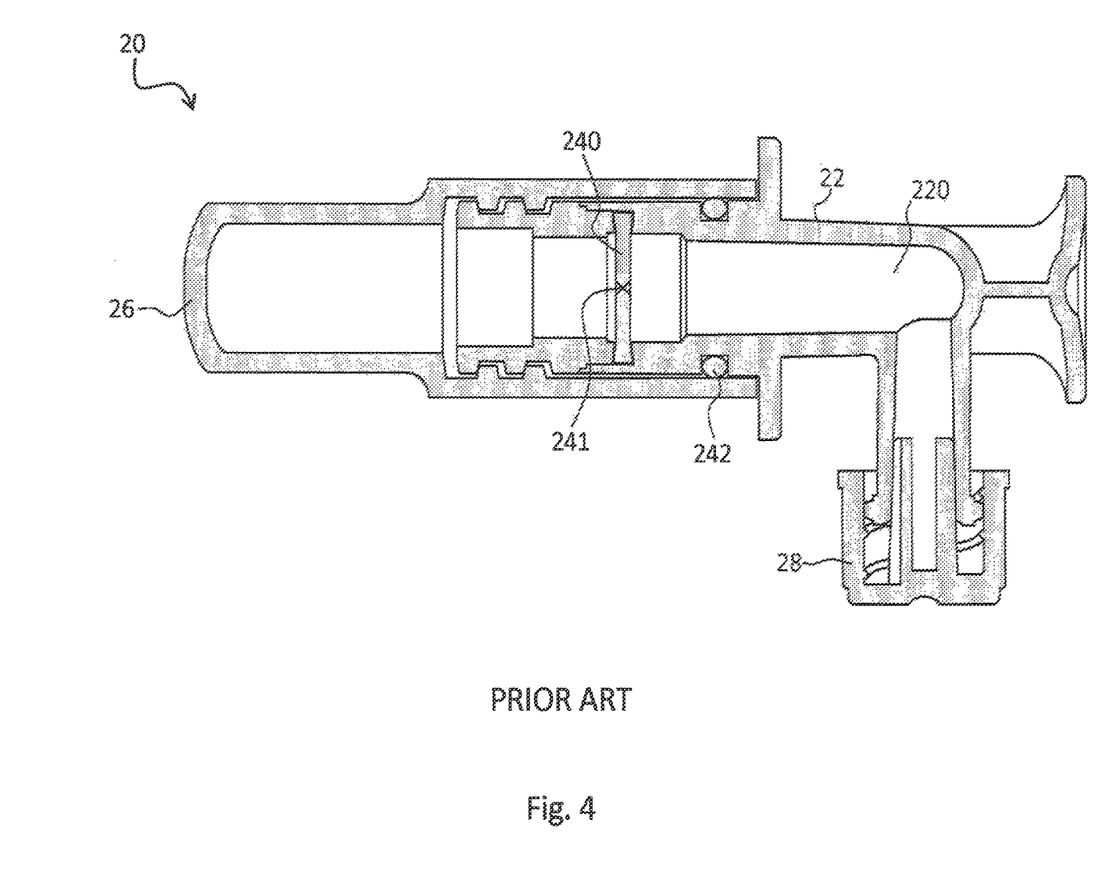
FIG. 4 schematically represents a cross section of a connector according to the prior art in a disconnected configuration.
Figure 5:
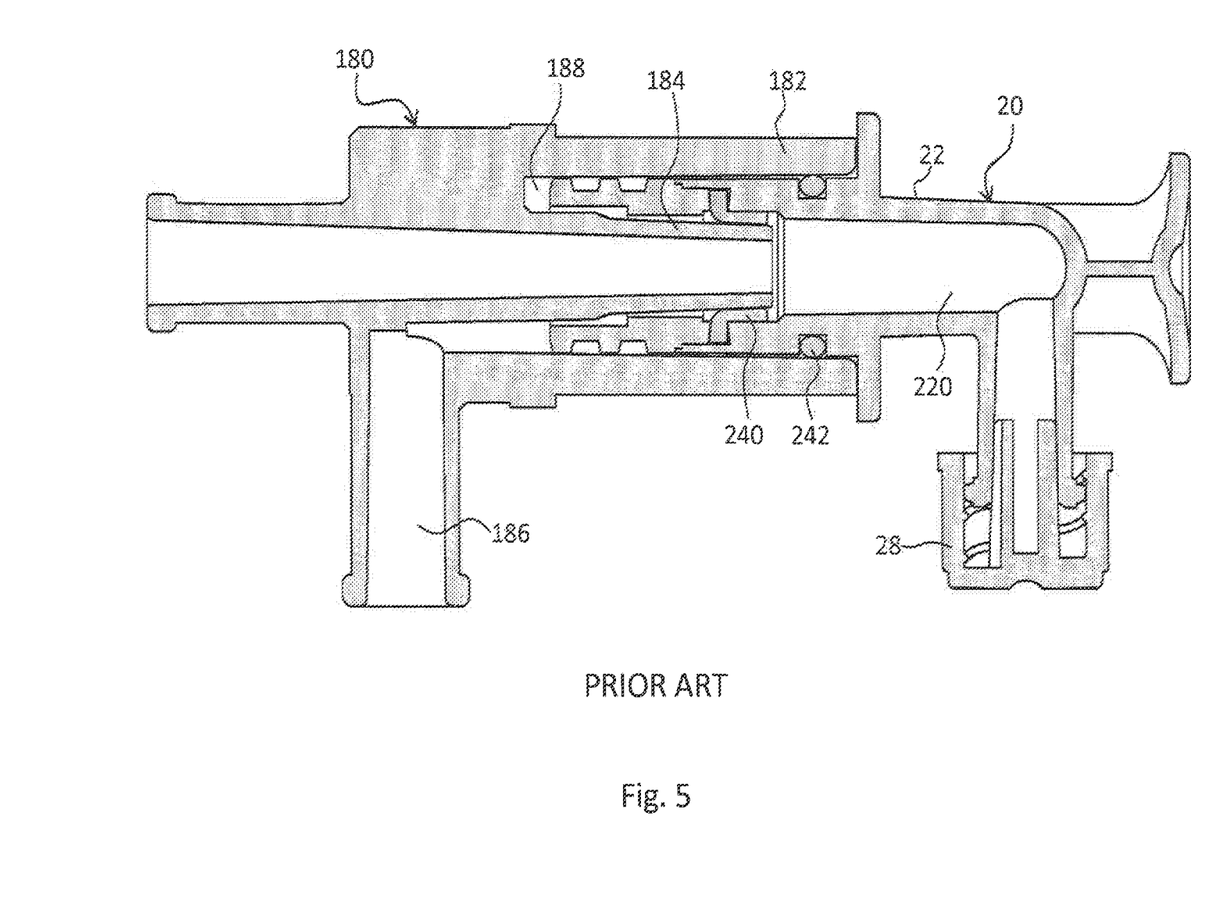
FIG. 5 schematically represents a cross section of the connector of FIG. 4 connected to the hemofiltration machine.

The substitution line of the disposable tubing set needs to be connected to the substitution port of the machine by means of a disposable connector. A disposable connector according to the prior art is shown in FIGS. 4 and 5. Such prior art connector, although widely used and appreciated, is not defect-free. It comprises four different components: a main body, a fixing thread, an o-ring seal, and a slotted membrane. In addition, the prior art connector comprises at least one removable cap or, in the most complicated version shown in FIG. 4, two removable caps. The main body and the fixing thread are usually obtained from polycarbonate or some other rigid material suitable for medical use. The o-ring seal and the slotted membrane are usually obtained from silicone or some other soft material suitable for medical use.

The assembly of the disposable connector of the known type requires that the membrane is inserted in its seat obtained along the duct of the main body, till it rests on the shoulder. Then also the fixing thread has to be inserted along the same duct, till it contacts the membrane. The main body and the fixing thread are then joined together by means of ultrasound welding, so as to hold the silicone membrane in place. The assembly of the known connector is then finished by slipping the o-ring seal along the main body to its seat and, in case, by putting on the two caps.

As can be easily appreciated by the skilled person, the prior art connector is quite complex and relatively expensive. The relatively high number of pieces, with respect to the overall dimensions of the connector, requires a time-consuming assembly. Moreover, the ultrasound welding step requires both dedicated equipments and qualified personnel.

The aim of the present invention is therefore to at least partially solve the drawbacks highlighted in relation to known connectors for hemofiltration treatments.

A task of the present invention is to provide a disposable connector having a simple structure, i.e. made of fewer components with respect to the known one. Another task of the present invention is to reduce the production and assembly costs of the disposable connector.

SUMMARY OF THE INVENTION

The aim and the tasks indicated above axe accomplished by a disposable connector as described herein.

BRIEF DESCRIPTION OF THE DRAWINGS

The characteristics and the further advantages of the invention shall become clear from the following description of some embodiments, given for indicating, and not limiting purposes with reference to the attached drawings, in which.

DETAILED DESCRIPTION OF THE PREFERRED EMBODIMENTS

Further scope of applicability of the present invention will become apparent from the detailed description given hereinafter. However, it should be understood that the detailed description and specific examples. While indicating preferred embodiments of the invention, are given by way of illustration only, since various changes and modifications within the spirit and scope of the invention will become apparent, to those skilled in the art from this detailed description.

Referring to the enclosed figures, the reference 20 indicates a disposable connector suitable for engagement on the substitution, port 180 of a hemofiltration machine 18. The connector 20 comprises: a rigid main body 22 defining a duct 220; and a soft element 24 fitted on an end of the main body 22. In the connector 20 according to the invention, the soft element 24 comprises a membrane 240 occluding the duct 220 and performing a valve function; and a seal portion 242 radially expanding outward of the duct 220.

In the attached figures, same references are used for elements which have same or similar functions, both in the connector according to the invention and in the one according, to the prior art.

The main body 22 is preferably obtained from polycarbonate (PC), acrylonitrile-butadiene-styrene (ABS), unplasticized polyvinyl chloride (uPVC) or some other rigid material suitable for medical use. The soft element 24 is preferably obtained from silicone, thermoplastic elastomer (TPE) or some other soft material suitable for medical use.

According to the embodiments shown in the attached FIGS. 6, 7, 9 and 12, the connector 20 according to the invention is, as a whole, L-shaped. Specifically, duct 220 defined by the main body 22 is L-shaped, having as main axis X and a secondary axis Y, see in particular FIG. 6. Conversely, according to the embodiment shown in the attached FIG. 13, the connector 20 according to the invention has a straight development. Specifically, duct 220 defined by the main body 22 has a straight development, having one axis X only. In the following description reference will be made principally to axis X. Consequently, except in case of explicit contrary indication, the term "axial" refers to the direction of a straight line parallel to axis X, the term "radial" refers to the direction of a half-line having its origin on axis X and perpendicular thereto, the term "circumferential" refers to the direction of a circumference having its centre on axis X and laying on a plane perpendicular thereto.

Figure 2:
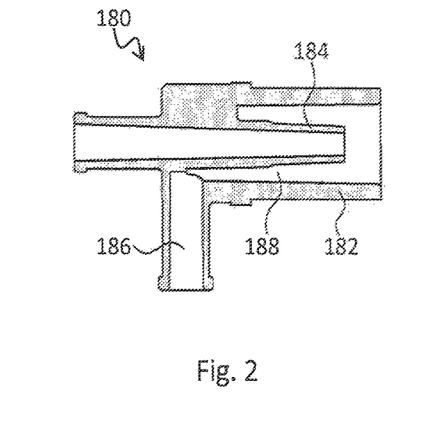
FIG. 2 schematically represents a lateral cross section of the substitution port of the hemofiltration machine in FIG. 1.
Figure 3:
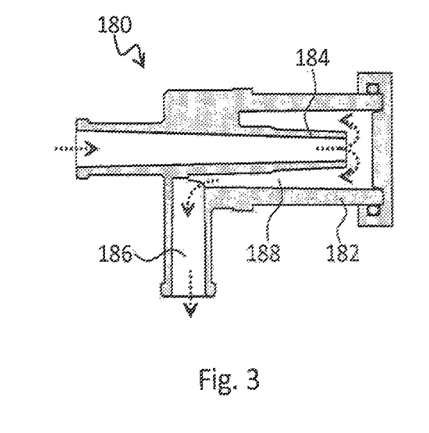
FIG. 3 schematically represents the port of FIG. 2 in a different configuration.

As can be noticed in FIGS. 2 and 3, the port 180 of the machine 18 comprises an inner cone 184 and a coaxial outer sleeve 182. The inner cone 184 defines a supply channel for the substitution liquid, while the outer sleeve 182 defines a protected interspace 188 around the inner cone 184. The outer sleeve 182 further defines a drain channel 186 which is used during the preparatory step for the hemofiltration treatment. Such step is schematically shown in FIG. 3 where the port 18 is closed by a proper plug. In such condition the substitution liquid cooling from the machine 18 is forced to circulate between the outer wall of the inner cone 184 and the inner wall of the outer sleeve 182, and then to flow out through the drain channel 186. Such circulation allows an accurate washing of the port 18, so as to assure hygiene of the connection.

According to some embodiments of the disposable connector 20, the membrane 240 is suitable for alternatively assuming a closed configuration or an open configuration. In particular, membrane 240 preferably assumes the closed configuration in a spontaneous manner, or at rest, i.e. in absence of any force directly acting upon it. See in this regard FIG. 6 wherein connector 20 is shown isolated, disengaged from the machine 18.

Conversely, membrane 240 assumes the open configuration after engagement of the connector 20 on the machine 18, in particular because of the specific conformation of the port 180 on which connector 20 is engaged. See in this regard FIG. 7 wherein connector 20 is shown engaged with port 180; it can be noticed that the inner cone 184 pushes the membrane 240, forcing it to the open configuration. In such condition duct 220 of connector 20 becomes an extension of the supply channel defined by the inner cone 184. Moreover, in the open configuration, the membrane 240 adheres on the outer wall of the inner cone 184, thus sealing the supply channel from the interspace 188. A successive disengagement of the connector 20 from the port 180, removing all the forces acting on the membrane 240, entails that the latter spontaneously assumes back its closed configuration, thus closing duct 220.

Figure 10:
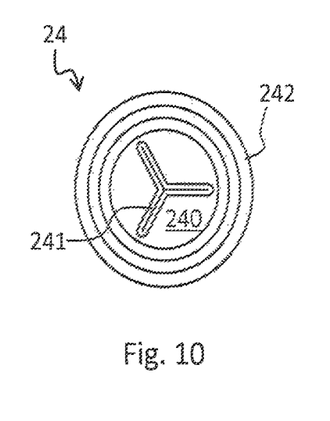
FIGS. 10 and 11 schematically represent two views of a detail of the connector according to the invention.
Figure 11:
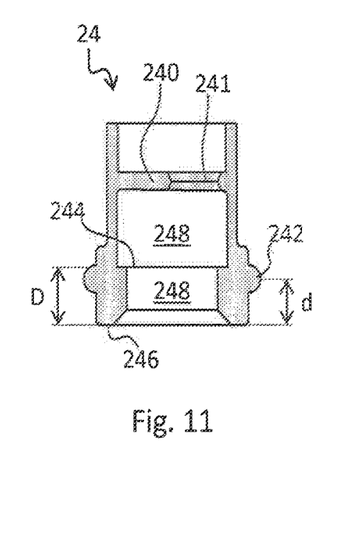

According, to some embodiments of the invention, e.g. the one shown in FIGS. 6, 7, 9 and 13, the membrane 240 comprises a simple diametrical slot 241. According to other embodiments of the invention, e.g. the one shown in FIGS. 10, 11 and 12, the membrane 240 comprises a V-shaped slot 241, i.e. a slot formed of three cuts extending radially from the center of the membrane and spaced by 120° one from the other.

As disclosed above, the soft element 24 comprises also a seal portion 242, intended to co-operate with the port 180 of the machine 18. In particular, the seal portion 242 is intended to make contact with the inner wall of the outer sleeve 182 so as to seal the interspace 188 from the outer environment. Engagement between connector 20 and port 180 of the machine 18 entails a slight interference between the seal portion 242 and the inner wall of the outer sleeve 182. As can be noticed in FIGS. 9 and 11, wherein the seal portion 242 is free from any contact, the seal portion 242 radially extends outward and has a substantially semicircular cross section. On the contrary in FIG. 7, wherein the seal portion 242 is constricted by the inner wall of the outer sleeve 182, the seal portion 242 has a smaller radial extension and a squashed cross section.

Figure 9:
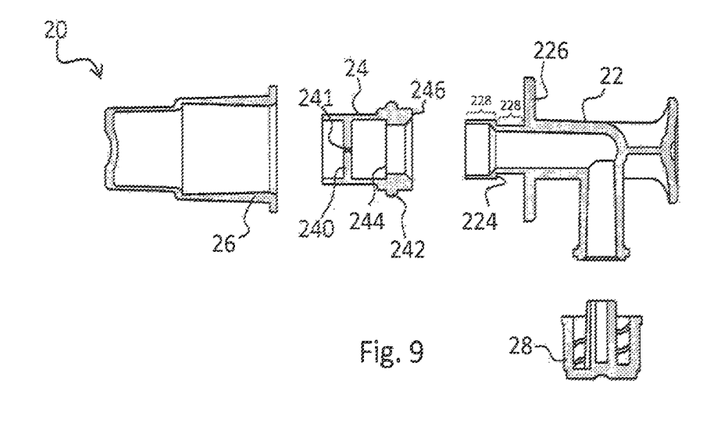
FIG. 9 represents an exploded lateral view of the connector of FIG. 6.

According to the embodiments shown in the attached figures, see in particular FIG. 9, the main body 22 comprises an undercut 224 and an axial shoulder 226 which radially extends outward. The undercut 224 is placed near the end of the main body 22 upon which the soft element 24 is fitted. Complementarily, the soft element 24 comprises a radial step 244 which protrudes inward. When the soft element 24 is forcedly fitted on the end of the main body 22, the axial end 246 of the soft element 24 contacts the shoulder 226 and the radial step 244 engages the undercut 224. In such a manner a shape coupling is established between the soft element 24 and the main body 22.

The shape coupling assures that the connector 20 remains firmly assembled during its use. According to some embodiments, such coupling is further strengthened by the specific shape of the soft element 24, or by the finish of the contact surfaces, or by both of them.

In particular, the coupling can be strengthened by the reciprocal positions of the radial step 244 and of the seal portion 242 with respect to the axial end 246. As can be noticed in FIG. 11, the distance D between the radial step 244 and the axial end 246 is longer than or equal to the distance it between the seal portion 242 and the axial end 246. When the connector 20 is engaged on the port 180, the specific relationship between D and d allows to exploit the radial pressure exerted by the outer sleeve 182 on the seal portion 242 in order to prevent the radial step 244 from any possible disengagement from the undercut 224 due to its deformation.

The coupling between the main body 22 and the soft element 24 can also be strengthened by the finish of the respective surfaces which contact each other. In particular, a very smooth surface finish entails a strong adhesion between the two surfaces. Accordingly, the contact zone 228 of the main body 22 (see FIG. 9) and the contact zone 248 of the soft element 24 (see FIG. 11) have very smooth surfaces, i.e. polished or lapped surfaces. As the skilled person will appreciate, since both the main body 22 and the soft element 24 are made of plastic materials, polishing and/or lapping treatments are actually carried out on the respective areas of the moulds, rather than on each single plastic piece.

Figure 6:
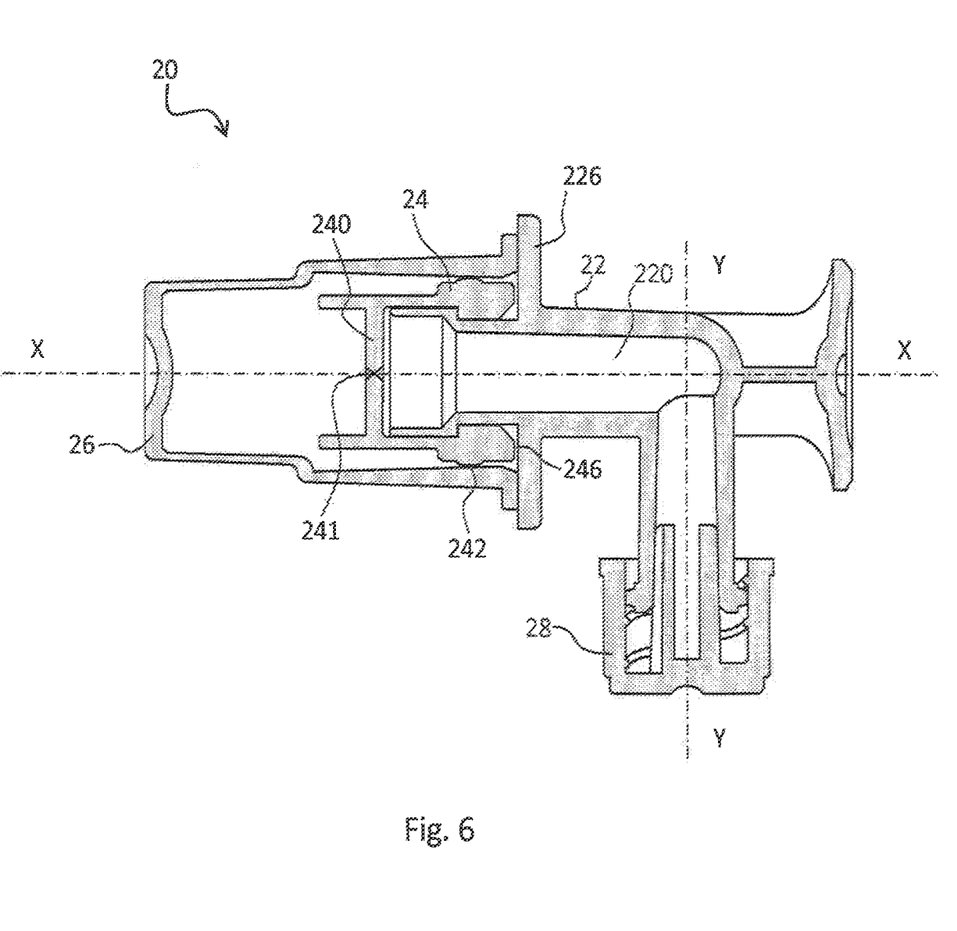
FIG. 6 schematically represents a cross section of a connector according to the invention in a disconnected configuration.
Figure 7:
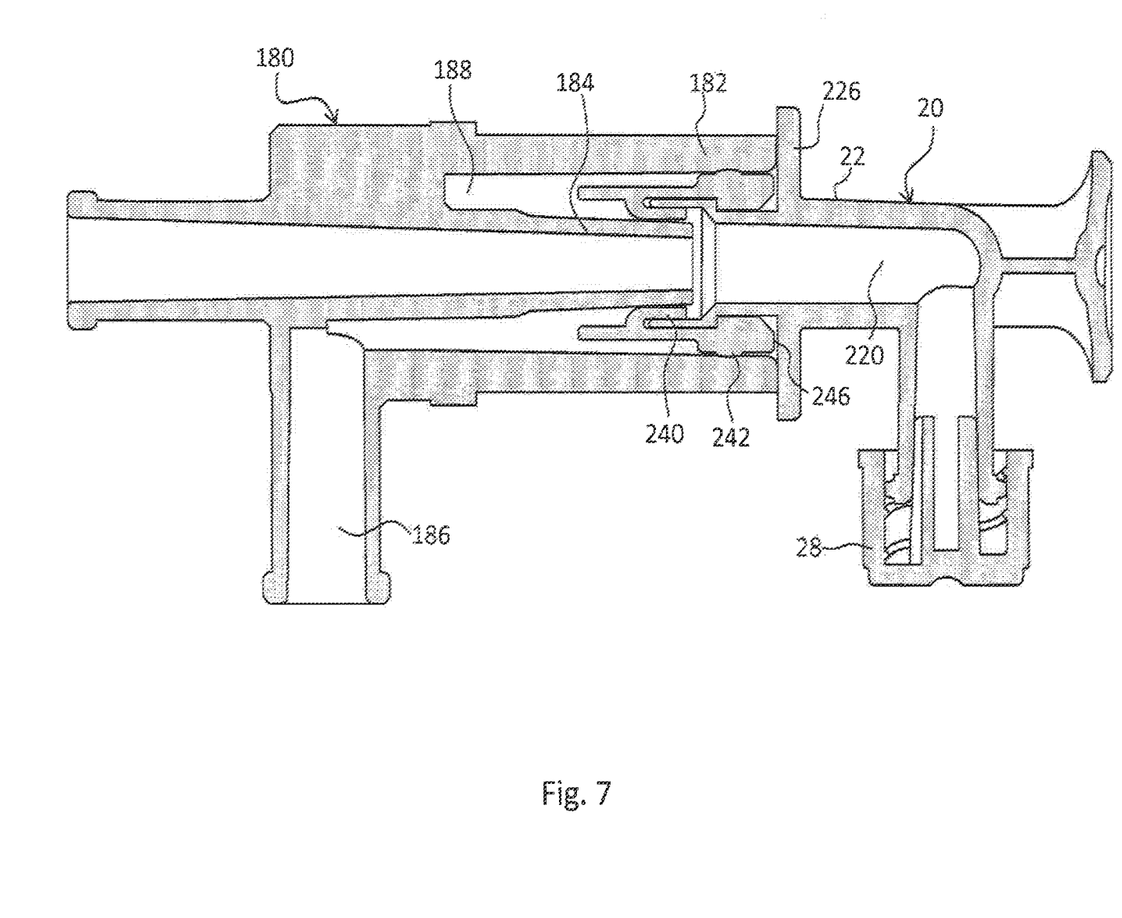
FIG. 7 schematically represents a cross section of the connector of FIG. 6 connected to the hemofiltration machine.
Figure 12:
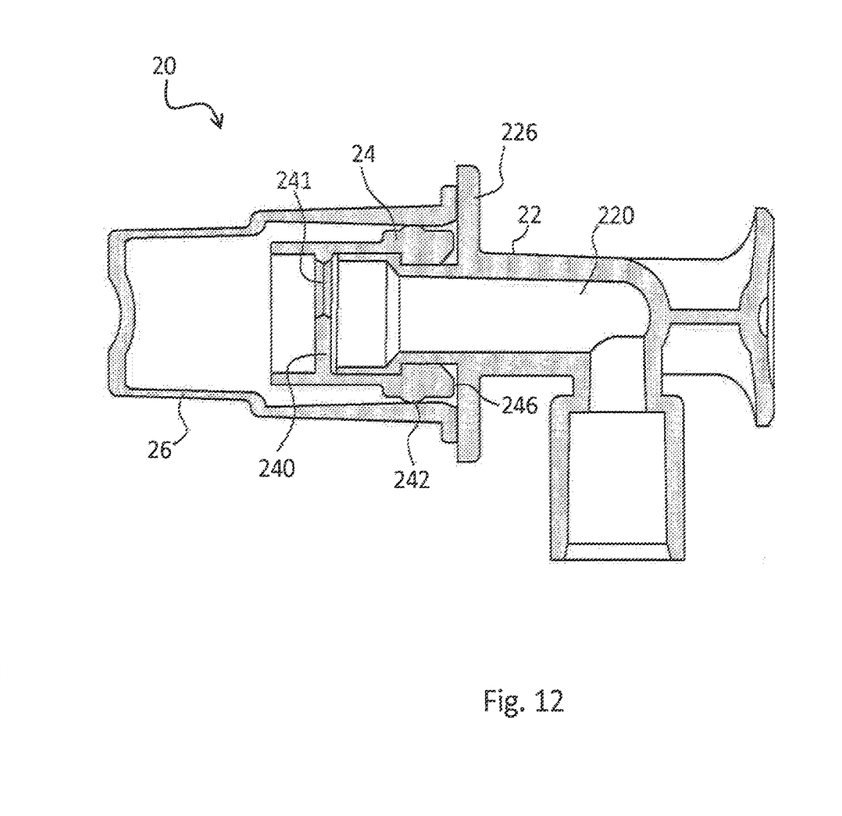
FIG. 12 schematically represents a cross section of a connector according to a different embodiment of the invention.
Figure 13:
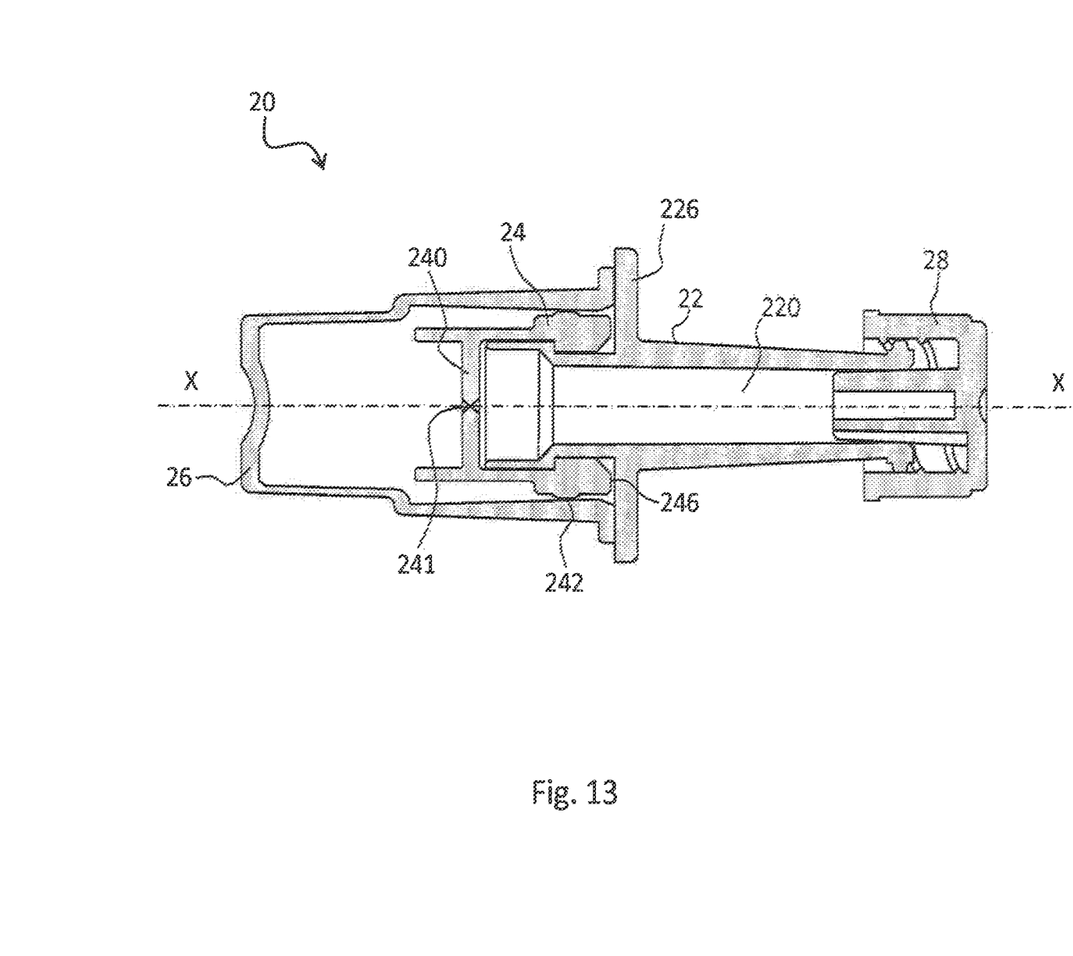
FIG. 13 schematically represents a cross section of a connector according to a different embodiment of the invention.

According to some embodiments, connector 20 further comprises one or two caps referenced to with 26 and 23 respectively. Such caps, which are suitable for plugging the ends of the duct 220, are intended to be removed before use. FIG. 6 shows the connector 20 with both caps 26 and 28. FIG. 7 shows the same connector 20 of FIG. 6 engaged on the port 180 and still having its cap 28 on. FIG. 12 shows a different embodiment of the connector 20 wherein only cap 26 is provided. Accordingly the other and of duct 220 is open and, in particular, is suitable for receiving a delivery tube to be glued therein.

Figure 8:
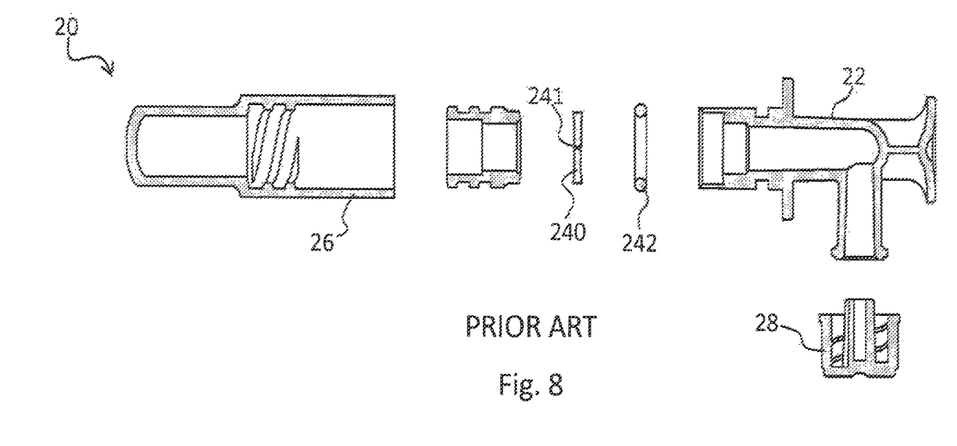
FIG. 8 represents an exploded lateral view of the connector of FIG. 4.

In view of the above description, the skilled person will easily appreciate that the present invention overcomes most of the drawbacks pointed out with respect to the prior art. In particular, the present invention provides a disposable connector having a simple structure, i.e. a disposable connector made of fewer components with respect to the known one. This can be further appreciated by comparison of FIG. 9, showing an exploded view of the connector according to the invention, with FIG. 8, showing an exploded view of the connector according to the prior art. Accordingly, the present invention reduces the production and assembly costs of the disposable connector, as a matter of fact, assembly of the connector according to the invention simply requires to fit the soft element 24 on the main body 22.

The person skilled in the art can bring modifications and/or replacements of described element with equivalent elements to the embodiments of the connector according to the invention described above, in order to satisfy specific requirements, without for this reason departing from the scope of the attached claims.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A connector for a substitution port of a blood treatment machine, said connector comprising:
   a main body defining a duct; and
   a pliable element that engages an end of the main body, the pliable element including a membrane that can occlude the duct, and
   a seal portion radially expanding outward of the duct, the seal portion having, in a non-contact state, a substantially semicircular cross section, and in a contact state, with the seal portion being constricted by a wall of the substitution port, a reduced radial extension and a compressed cross section.

2. The connector according to claim 1, wherein the connector is substantially L-shaped and the duct is substantially L-shaped.

3. The connector according to claim 1, wherein the connector is configured to engage the substitution port of the machine having an inner cone defining a supply channel for a substitution liquid, and a coaxial outer sleeve defining a protected interspace around the inner cone.

4. The connector according to claim 3, wherein the membrane is configured to alternatively assume a closed configuration or an open configuration.

5. The connector according to claim 4, wherein the membrane assumes the closed configuration at rest in an absence of any force directly acting upon the membrane.

6. The connector according to claim 4, wherein the membrane assumes the open configuration after engagement of the connector with the substitution port, due to the inner cone forcing the membrane to the open configuration.

7. The connector according to claim 4, wherein, in the open configuration, the membrane adheres to an outer wall of the inner cone to seal the duct from the interspace.

8. The connector according to claim 1, wherein the membrane includes a diametrical slot.

9. The connector according to claim 1, wherein the membrane includes a Y-shaped slot.

10. The connector according to claim 3, wherein the seal portion is configured to contact the inner wall of the outer sleeve of the substitution port so as to seal the interspace from the outer environment.

11. The connector according to claim 1, wherein
    the main body includes an undercut near an end thereof, and an axial shoulder radially extending outward therefrom, and
    the pliable element includes an axial end and a radial step protruding inward such that when the pliable element is forcedly fitted on the end of the main body, the axial end of the pliable element contacts the axial shoulder and the radial step engages the undercut so as to establish a shape coupling between the pliable element and the main body.

12. The connector according to claim 11, wherein, for the pliable element, a distance D between the radial step and the axial end is longer than or equal to a distance d between the seal portion and the axial end.

13. The connector according to claim 1, wherein the main body includes a contact zone and the pliable element includes a contact zone, and wherein the contact zone of the main body and the contact zone of the pliable element have polished or lapped surfaces.

14. The connector according to claim 1, further comprising a first cap and a second cap configured to plug each respective end of the duct, and to be removed before use.

15. The connector according to claim 1, further comprising a cap configured to plug an end of the duct and to be removed before use, and wherein another end of the duct is open and is configured to receive a delivery tube to be adhered thereto.

16. The connector according to claim 1, wherein the main body is rigid.

17. The connector according to claim 1, wherein the main body and the pliable element engage via a shape coupling.

18. The connector according to claim 1, wherein the connector is configured to engage the substitution port of a hemofiltration machine or a hemodiafiltration machine.

19. A connectable assembly for a blood treatment machine, said connectable assembly comprising:
a substitution port of the blood treatment machine; and
a connector for connection with the substitution port, the connector including
a main body defining a duct, and
a pliable element that engages an end of the main body,
the pliable element including a membrane that can occlude the duct, and
a seal portion radially expanding outward of the duct, the seal portion having, in a non-contact state, a substantially semicircular cross section, and in a contact state, with the seal portion being constricted by a wall of the substitution port, a reduced radial extension and a compressed cross section.

20. The connectable assembly according to claim 19, wherein the membrane is configured to alternatively assume a closed configuration or an open configuration.

21. The connectable assembly according vo claim 19, wherein with the substitution port and the connector in a connected configuration, the membrane has an open configuration.

* * * * *